United States Patent [19]
Kawano

[11] Patent Number: 6,123,665
[45] Date of Patent: Sep. 26, 2000

[54] ENDOSCOPE APPARATUS AND SURGICAL INSTRUMENT THEREFOR

[75] Inventor: Hironobu Kawano, Tokyo, Japan

[73] Assignee: Olympus Optical Co., Ltd., Tokyo, Japan

[21] Appl. No.: 09/124,015

[22] Filed: Jul. 29, 1998

[30] Foreign Application Priority Data

Jul. 30, 1997 [JP] Japan ................................. 9-203660

[51] Int. Cl.[7] ............................. A61B 1/18; A61B 17/00
[52] U.S. Cl. ....................... 600/104; 600/106; 606/110; 606/113; 606/47
[58] Field of Search ..................... 600/104, 105, 600/106, 153, 156; 604/272; 606/47, 110, 113

[56] References Cited

U.S. PATENT DOCUMENTS

| | | | |
|---|---|---|---|
| 4,503,855 | 3/1985 | Maslanka | 606/47 |
| 4,718,419 | 1/1988 | Okada | 606/47 |
| 5,122,147 | 6/1992 | Sewell, Jr. | 606/110 |
| 5,190,542 | 3/1993 | Nakao et al. | 606/47 |
| 5,312,418 | 5/1994 | Bonnet | 606/128 |
| 5,336,227 | 8/1994 | Nakao et al. | 606/114 |
| 5,376,094 | 12/1994 | Kline | 606/113 |
| 5,535,759 | 7/1996 | Wilk | 128/898 |
| 5,542,948 | 8/1996 | Weaver et al. | 606/113 |
| 5,846,248 | 12/1998 | Chu et al. | 606/114 |

FOREIGN PATENT DOCUMENTS

| | | |
|---|---|---|
| 51-53672 | 12/1976 | Japan . |
| 5-212045 | 8/1993 | Japan . |

*Primary Examiner*—John P. Leubecker
*Attorney, Agent, or Firm*—Morgan, Lewis & Bockius LLP

[57] ABSTRACT

In a surgical instrument for endoscopes, one end of a resecting section of a wire to be used for resecting a lesion is fixedly connected to a fluid injection needle, and the other end of the same is fixedly connected to a surgical instrument operation section. As a result, the retraction of the fluid injection needle and the resection of the lesion can be carried out by means of a single operation for sliding the treatment instrument operation section.

36 Claims, 4 Drawing Sheets

ENDOSCOPE APPARATUS AND SURGICAL INSTRUMENT THEREFOR

BACKGROUND OF THE INVENTION

1. Field of the Invention

The present invention relates generally to an endoscope apparatus and, more particularly, to a surgical instrument for the endoscope used for strip biopsy surgery.

2. Related Art

Generally, a small protruding lesion formed in the body cavity is resected by inserting a high-frequency resecting tool from a forceps channel of an endoscope, by fitting a incising loop made of a metal wire around the protruding lesion, and by applying a high frequency to the incising section. However, many small lesions do not involve a protuberance, making it impossible to fit the incising loop around the lesion.

For this reason, there has been recently developed so-called a strip biopsy surgery. In this operation, a physiological salt solution is poured into a non-protruding lesion through use of an endoscopic syringe, as disclosed in Japanese Utility Model No. Sho-51-53672, thereby causing the lesion to protrude beforehand. The incising loop of the high-frequency resecting tool is fit around the thus-protruded lesion, thereby incising the lesion at high frequencies.

Unexamined, published Japanese Patent Application No. Hei-5-212045 describes a surgical instrument for endoscopes having a sheath which permits the high-frequency resecting tool and the endoscopic syringe to move back and forth independently of each other. The surgical instrument of this type is not required to be inserted into or removed from the forceps channel for respective operations for pouring a physiological salt solution and for incising a lesion using high frequencies. As a result, the overall operations required by the strip biopsy can be simplified, and the efficiency of the operations can be improved.

FIGS. 5A and 5B are a perspective and a transverse cross-sectional views, respectively, showing the configuration of the distal end portion of the surgical instrument for endoscopes. As shown in FIGS. 5A and 5B, the surgical instrument 1 for endoscope is provided with a sheath 2 which is a flexible tube and has an external diameter to be fitted into the forceps channel of the endoscope. The sheath 2 is formed from an electrically insulating material.

The inside of the sheath 2 is partitioned by means of a partition wall 2c into two tubes 2a and 2b, each of which has a substantially semicircular cross section. The flexible tube 3 is inserted into the first tube 2a so that it moves back and forth by way of manual operations. A fluid injection needle 4 is fixed to a tip end of the tube 3, and a socket not shown which permits receipt of a syringe (e.g., a fluid supply member) is coupled to the handgrip end of the tube, thereby forming a syringe needle which permits injection of a physiological salt solution into the tissue of the body cavity.

The high-frequency resecting tool 5 is inserted into the second tube 2b so that it moves back and forth independently of the tube 3 by way of manual operations. A metal wire 6, which is widely bent at the front end thereof to form a loop, is attached to the high-frequency resecting tool 5. The loop-shaped part of the wire 6 performs as an incising section 7.

The wire 6, which is bent at its front end thereof, extends to the handgrip side of the surgical instrument for endoscope through the second 2b of the sheath 2, and can slidably moves back and forth therein by way of manual operations.

The operation of the surgical instrument 1 for endoscope having the foregoing configuration will now be described. First, the flexible tube 3 is inserted into the first tube 2a of the sheath 2, and the high-frequency resecting tool 5 is inserted into the second tube 2b. Further, the surgical instrument 1 for endoscope is inserted into the body cavity through manual operations by way of the forceps channel while the incising section 7 provided at the end of the resecting tool 5 and the fluid injection needle 4 secured to the distal end of the tube 3 are housed within the sheath 2.

While the leading end of the sheath 2 of the surgical instrument 1 for endoscope is guided to the vicinity of the lesion of tissue, the resecting section 7 is operated to protrude from the distal end of the sheath 2 through manual operations, so that the loop-shaped resecting section 7 comes to locate at the periphery of the lesion.

Under this condition, the tube 3 is forcefully pushed through manual operations, and the fluid injection needle 4 is stuck into the lesion. A physiological salt solution is poured into the lesion by means of the syringe. As a result of the foregoing operations, the lesion is protruded, and the thus-protruding lesion is inserted into the loop of the incising section 7, so that the protruding lesion is fitted into the incising section 7.

Next, the fluid injection needle 4 is retracted into the sheath 2 by manually pulling back the tube 3 and, thereafter, the incising section 7 is closed by manually retracting the wire 6 independently from the pulling-back operation of the tube 3, thereby tightly tying the lesion. Subsequently, a high frequency is applied to the wire 6 and the incising section 7 thereof from a high frequency power supply (not shown), thereby resecting the lesion.

In the conventional surgical instrument for endoscope, as described above, the fluid injection needle and the resecting tool are arranged to slide back and forth in the sheath independently of each other. At the time of a strip biopsy, a lesion must have been tied by means of the incising section of the resecting tool only after the fluid injection needle has been retracted into the sheath after a physiological salt solution has been poured into the lesion. In this way, the operator is required to perform retracting operations twice, thus deteriorating the operability of the surgical instrument for endoscope.

SUMMARY OF THE INVENTION

The present invention has been conceived in view of the foregoing problems, and an object of the present invention is to provide an endoscope apparatus and a surgical instrument for the endoscope apparatus which is capable of improving the operability of the surgical instrument for endoscope. Another object of the present invention is to provide an endoscope apparatus and a surgical instrument for the endoscope apparatus capable of accomplishing the strip biopsy operation which requires merely a single retracting operation.

To this end, according to one aspect of the present invention, there is provided a surgical instrument for endoscope comprising: a flexible sheath; a flexible tube which is inserted into the flexible sheath so as to be able to move back and forth through operations of an instrument operation section provided at a handgrip-end of the sheath and which has at the front end a fluid injection needle and has at a handgrip end a fluid supply section; and an resecting tool which is fixed at one end to the fluid injection needle and is fixed at the other end to the instrument operation section so as to be able to move back and forth simultaneous with the tube and which is provided with a metal wire having at the front end an incising section.

In the surgical instrument for endoscope according to the present invention, an injection needle is retracted at the same time of the resecting tool tying and incising a lesion by a single operation after a fluid has been injected into the lesion by way of the fluid injection needle to thereby cause the lesion to protrude and after the protruding lesion has been fit into the resecting tool.

DESCRIPTION OF THE PREFERRED EMBODIMENT

Figure 1:
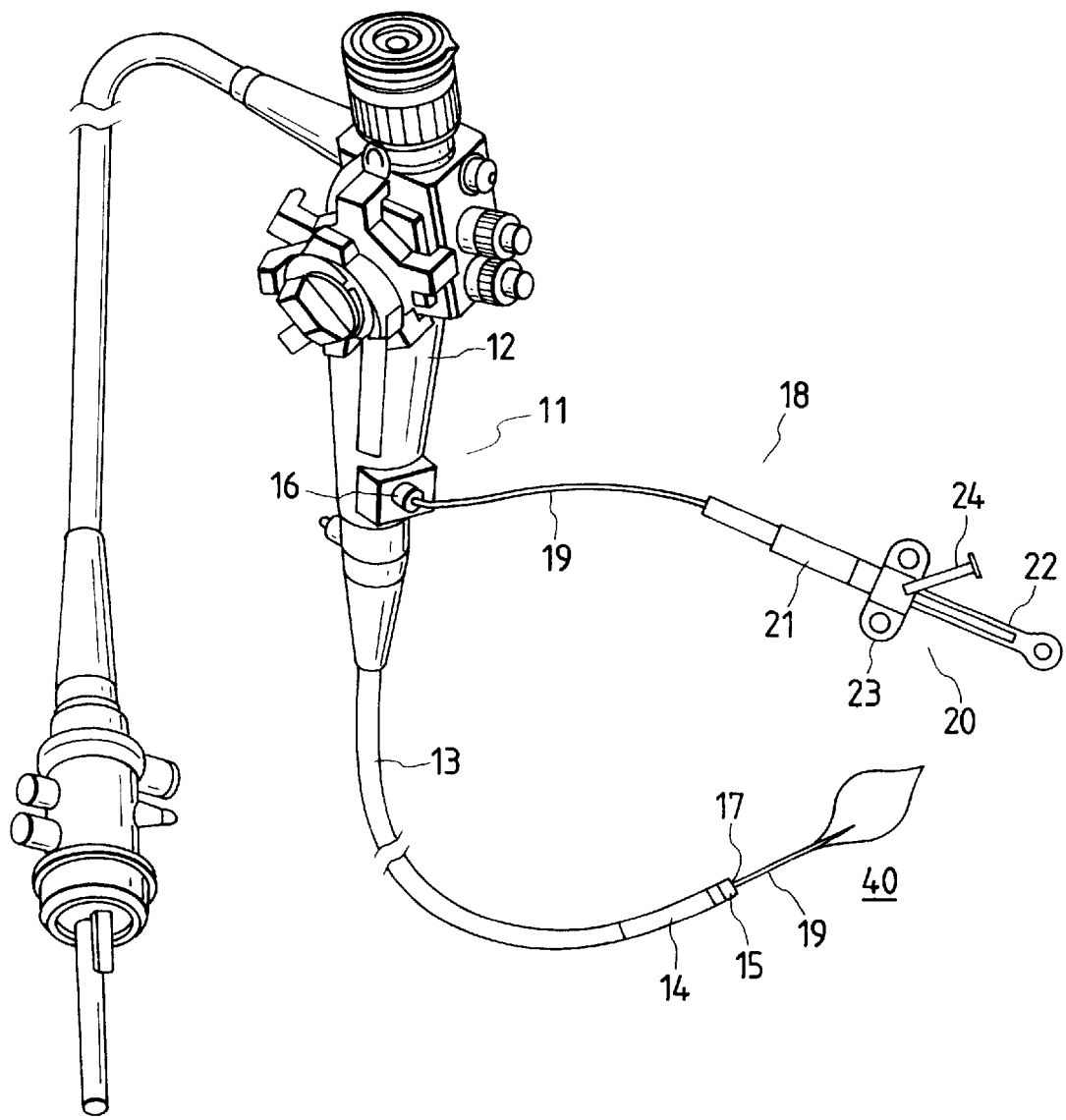
FIG. 1 is an external view showing a surgical instrument for endoscope according to a preferred embodiment of the present invention.
Figure 2:
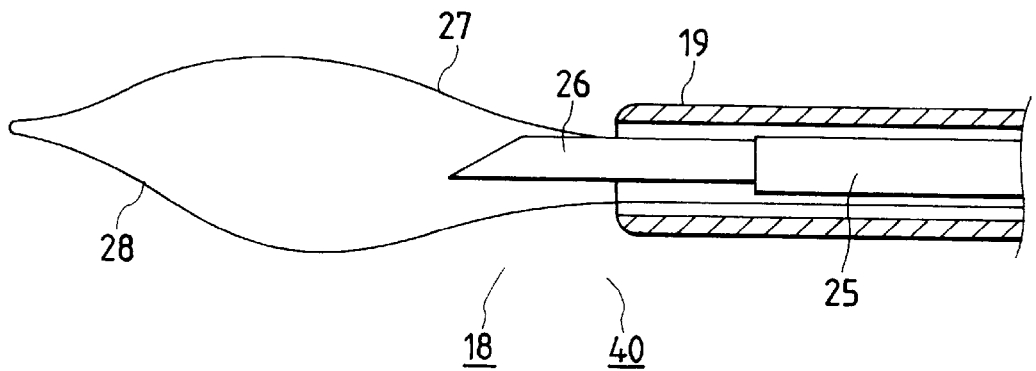
FIG. 2 is a longitudinal cross-sectional view showing a distal end of the surgical instrument for endoscope according to the present embodiment.
Figure 3A:
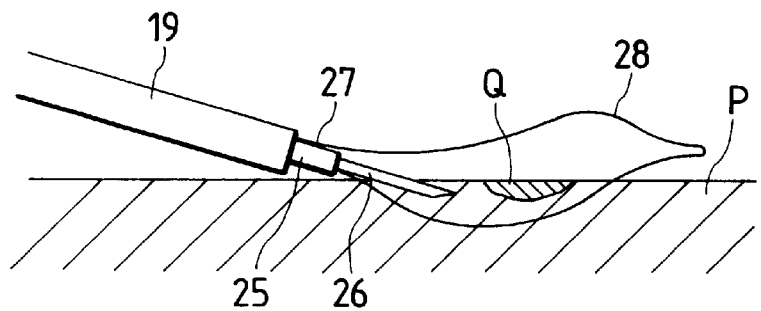
FIGS. 3A, 3D and 3C are views showing the operation steps of the surgical instrument for endoscope according to the present embodiment when it is used.

A preferred embodiment of the present invention will now be described by reference to FIGS. 1 through 3. FIG. 1 is a schematic view showing an endoscope apparatus with a surgical instrument for endoscope according to one embodiment of the present invention when the instrument is coupled a forceps channel of the endoscope apparatus, and FIG. 2 is a longitudinal cross-sectional view showing an enlarged distal end portion of the surgical instrument for endoscope according to the present embodiment. FIGS. 3A, 3B and 3C are explanatory views showing steps of using the surgical instrument for endoscope according to the present embodiment.

As shown in FIG. 1, an endoscope apparatus 11 is provided with an operation section 12 at the handgrip end thereof and an insertion section 13 formed from a flexible tube engaging with the operation section 12. An end structure section 15 is coupled to the insertion section 13 by way of a curved section 14 for curving operation purposes.

At the handgrip end of the operation section 12 there is provided a forceps insert socket 16 together with a curved operation knob, an air-and-water feed button, a suction button, and an eyepiece. One end of a channel not shown provided in the endoscope 11 connects to the forceps insert socket 16, and the other end of the forceps channel couples to a forceps socket 17 formed in the end structure section 15.

A surgical instrument 18 for endoscope according to the present invention is provided with a sheath 19 inserted into the forceps channel through the forceps insert socket 16 of the endoscope apparatus 11. The sheath 19 is constituted by a tube made of polymeric resin having an electrical insulating property such as, for example, PTFE and FEP. The sheath 19 is designed to have flexibility sufficient to enter the forceps channel.

At the handgrip end of the surgical instrument 18 for endoscope 18 there is provided a surgical instrument operation section 20. A guide 22 extends longitudinally from an operation section body 21 of the instrument operation section 20. A slider 23 is attached to the guide 22 to be slidable in a longitudinal direction thereof. A cock 24 protrudes from the side of the slider 23, and a syringe not shown for injecting a fluid, such as a physiological salt solution, is to be attached to the cock 24.

The configuration of the distal end portion of the surgical instrument 18 for endoscope thus provided will be described in detail with reference to FIG. 2.

A flexible tube 25 disposed inside the sheath 19 forms a channel for permitting flow of a fluid such as a physiological salt solution. The flexible tube 25 is formed from polymeric resin such as PTFF, FEP and the like. The flexible tube 25 may be formed from a material having an electrically insulating property. A fluid injection needle 26 is fixedly attached to the distal end portion of the flexible tube 25. Further, the handgrip end portion of the flexible tube 25 extends up to the surgical instrument operation section 20 and is fixedly coupled to the cock 24. Hence, a fluid can be poured into the flexible tube 25 from a syringe or the like fitted to the cock 24. Further, by sliding the slider 23 on the guide 22, the flexible tube 25 and the fluid injection needle 26 can be operated to protrude from or retract into the end opening of the sheath 19.

One end of a metal wire 27 formed from a single or stranded wire connects to the fluid injection needle 26 by, e.g., brazing, soldering, or adhesion by an adhesive. The end part of the wire 27 is imparted with a property of spreading into a substantially elliptical shape thereby constituting an resecting section 28, so that the resecting section 28 spreads like a loop when it protrudes from the end opening of the sheath 19. The other end of the wire 27 passes through the sheath 19 and secured to the slider 23 of the surgical instrument operation section 20. The resecting section 28 can be retracted into the sheath 19 by sliding the slider 23 on the guide 22.

In short, when the slider 23 is operated to slide along the guide 22, both the fluid injection needle 26 and the resecting section 28 are actuated to protrude from and retract into the end opening of the sheath 19 at the same time. The end portion of the sheath 19, the fluid injection needle 26 and the resecting section 28 of the wire 27 constitute a surgical section 40.

The operation of the surgical instrument for endoscope having the foregoing configuration will now be described with reference to FIGS. 3A, 3B, and 3C.

First, the flexible tube 25 used for injecting a fluid and the wire 27 are inserted into the sheath 19. Further, the slider 23 of the surgical instrument operation section 20 is pulled back toward an operator. While the fluid injection needle 26 secured to the distal end of the flexible tube 25 and the resecting section 28 provided at the end portion of the wire 27 are retracted into the sheath 19, the surgical section 40 of the surgical instrument 18 for endoscope is inserted into the body cavity through the forceps channel of the endoscope apparatus 11.

While the distal end of the sheath 19 of the surgical instrument 18 for endoscope is guided to the vicinity of a lesion Q of tissue P, the slider 23 is pushed forward along the guide 22. As a result, as shown in FIG. 3A, the fluid injection needle 26 is stuck into the area of the lesion Q facing the surgical instrument for endoscope. A physiological salt solution R is poured into the lesion Q from a syringe fitted to the cock 24.

Figure 3B:
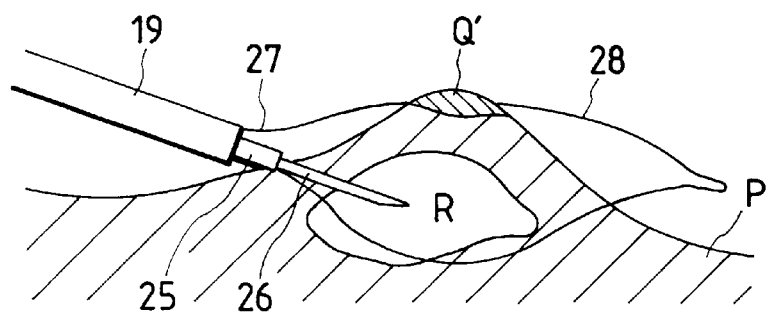

Next, as shown in FIG. 3B, a lesion Q', which has protruded as a result of the injection of a physiological salt water R, is fitted into the loop shaped resecting section 28.

Figure 3C:
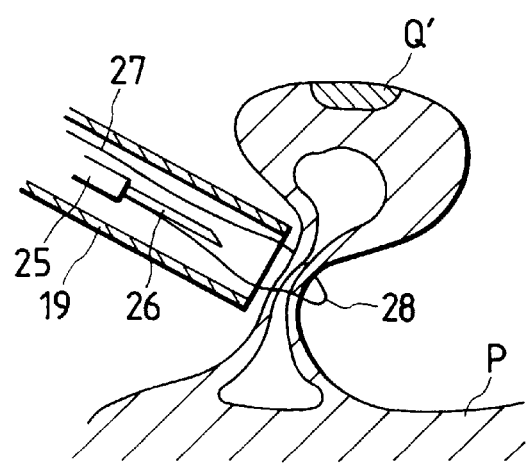
Figure 5A:
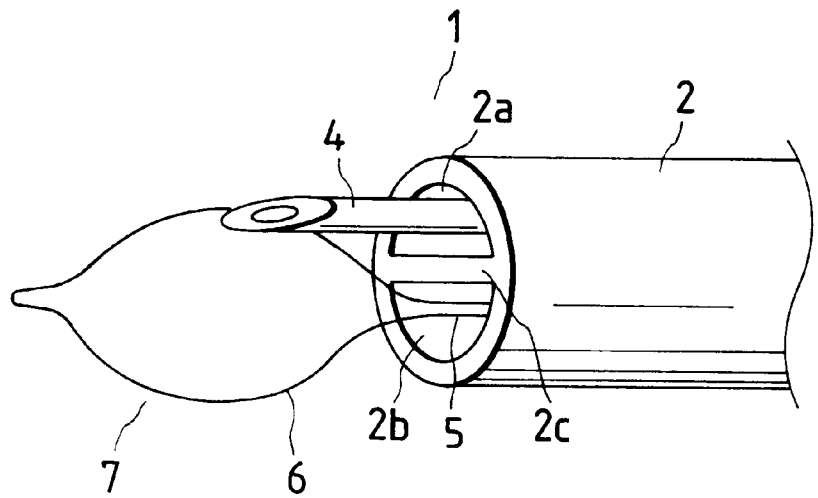
FIG. 5A is a perspective view showing a distal end part of the conventional surgical instrument for endoscope.
Figure 5B:
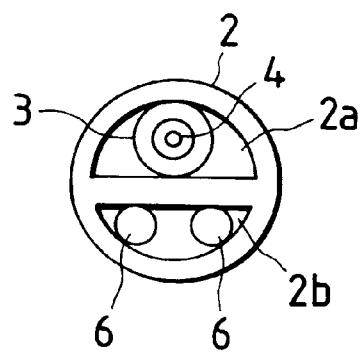
FIG. 5B is a transverse cross-sectional view thereof.

Next, as shown in FIG. 3C, the slider 23 is operated to slide back along the guide 22 toward the operator, whereby the fluid injection needle 26 and the resecting section 28 are retracted into the sheath 19 at the same time, thus resecting the lesion Q'. On example of resecting the lesion employs a certain level of high frequency energy supplied to the wire 27 from a high frequency generation device.

As described above, the surgical instrument for endoscope according to the present embodiment enables operations for resecting a lesion after having injected a fluid into the lesion and for removing the fluid injection needle by way of a single sliding operation of the slider 23. Accordingly, the operations are simplified, and the efficiency of strip biopsy can be improved.

Figure 4:
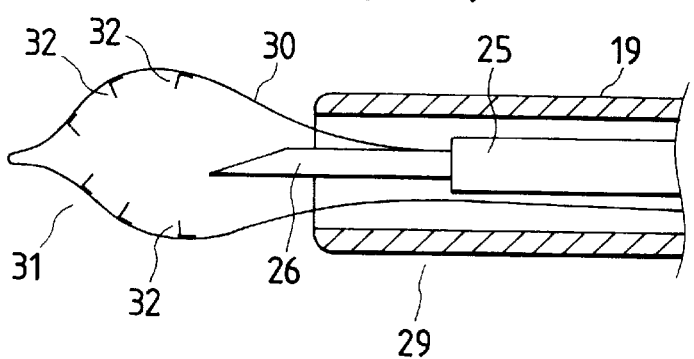
FIG. 4 is a longitudinal cross-sectional view showing a modification of the embodiment of the present invention.

One modification of the present embodiment will now be described with reference to FIG. 4. FIG. 4 is a longitudinal cross-sectional view showing the configuration of the distal end of a surgical instrument for endoscope according to a modification of the present embodiment. The same parts and components used in the foregoing embodiment and that of the modification are assigned the same reference numerals, and their explanations will be omitted here for brevity.

One end of a metal wire 30 formed from a single or stranded wire is fixedly connected to the fluid injection needle 26 secured to the distal end of the flexible tube 25 which is provided in the sheath 19 of a surgical instrument 29 for endoscope.

Slip-prevention members 32, which are small pins or needles, are provided at intervals along the inside of an resecting section 31 of the wire 30 which is imparted with a property of spreading into a substantially elliptical loop such a way as to protrude toward the center of the resecting section. The other end of the wire 30 is fixedly connected to the slider of the surgical instrument operation section, as in the case of the wire in the foregoing embodiment. The slip-prevention members 32 may be formed separately from the wire, and attached to the wire before the surgical instrument is assembled.

According to the modified embodiment, when the resecting section 30 is fitted around a lesion that has been protruded, the resecting section can be prevented from slipping and, therefore, the operability of the surgical instrument can be improved more.

According to the preferred embodiment of the invention as described above, one end of the wire 27, 30 is connected to the fluid injection needle 26 while the other end of which is connected to the slider 23 of the surgical instrument operation section 20. However, the invention is not limited thereto or thereby. For example, both the ends of the wire may be fixedly connected to the slider 23 of the surgical instrument operation section 20 to accomplish the purpose of the invention. The important point is, the wire should be connected to any part which moves or slides relative to the sheath 19 and to which high frequency can be applied.

Further, the fluid injection needle 25 may be formed from a material having a certain rigidity to make a sharp tip. One example of the material of the needle is metal, though the invention is not limited thereto.

As has been mentioned above, the surgical instrument for endoscope according to the present invention enables operations for resecting a lesion after having injected a fluid into the lesion and for removing the fluid injection needle by way of a single sliding operation. As a result, operations can be simplified, and the efficiency of operations required by strip biopsy can be improved.

What is claimed is:

1. A surgical instrument for endoscope, comprising:
an operation section having a base part and a single movable part which is movable relative to the base part;
an elongated and flexible hollow member having a first end coupled to said operating section and a second end for insertion into a body cavity;
a flexible fluid passage forming member disposed in said hollow member to be slidable relative thereto, a tip end of the fluid passage forming member protruding from and retracting in the second end of the hollow member when the single movable part of the operation section moves in the hollow member relative to the base part thereof; and
a resecting member disposed within the hollow member, at least one end of the resecting member being engageable with the single movable part which moves relative to the base part of the operation section, the resecting member comprising a loop forming part when it protrudes from the hollow member;
wherein movement of the single movable part in a first direction protrudes both the tip end of the fluid passage forming member and the resecting member from the hollow member and movement of the single movable part in a second direction retracts both the tip end of the fluid passage forming member and the resecting member into the hollow member.

2. The surgical instrument according to claim 1, wherein:
said base part of said operation section comprises a guide member extending from an operation section body in a longitudinal direction thereof and the movable part comprises a slider mounted on the guide member slidably in the longitudinal direction thereof;
said hollow member comprises a tube-like sheath; and
said fluid passage forming member comprises a fluid injection needle and a tube member extending from the operation section to the second end of the hollow member, an end of said tube member is secured to the slider of the operation section and the other end of which fixedly connects the fluid injection needle.

3. The surgical instrument according to claim 1 or 2, wherein the resecting member comprises a metal wire.

4. The surgical instrument according to claim 3, wherein the wire is formed from a single wire.

5. The surgical instrument according to claim 3, wherein the wire is formed from a stranded wire.

6. The surgical instrument according to claim 3, wherein the wire connects to the fluid injection needle by brazing.

7. The surgical instrument according to claim 3, wherein the wire connects to the fluid injection needle by soldering.

8. The surgical instrument according to claim 3, wherein the wire connects to the fluid injection needle by adhesion by an adhesive.

9. The surgical instrument according to claim 3, wherein the wire is widely bent at the front end thereof to form a loop.

10. The surgical instrument according to claim 2, wherein the sheath is formed from an electrically insulating polymeric resin material.

11. The surgical instrument according to claim 2, wherein the sheath is formed from a polymeric resin.

12. The surgical instrument according to claim 1, wherein both ends of said resecting member engage with the movable part of the operation section.

13. The surgical instrument according to claim 1, wherein the resecting member comprises at least one slip-prevention member along the inside thereof.

14. The surgical instrument according to claim 13, wherein the slip-prevention member comprises a small pin provided at intervals.

15. The surgical instrument according to claim 13, wherein the slip-prevention member comprises a small needle provided at intervals.

16. The surgical instrument according to claim 1, wherein a high frequency energy is applied to the resecting member.

17. A surgical instrument for endoscope, comprising:
an operation section having a base part and a movable part which is movable relative to the base part;
an elongated and flexible hollow member having a first end coupled to said operating section and a second end for insertion into a body cavity;
a flexible fluid passage forming member disposed in said hollow member to be slidable relative thereto, a tip end of the fluid passage forming member protruding from and retracting in the second end of the hollow member when the movable part of the operation section moves in the hollow member relative to the base part thereof; and
a resecting member disposed within the hollow member, at least one end of the resecting member being engageable with the movable part which moves relative to the base part of the operation section, the resecting member comprising a loop forming part when it protrudes from the hollow member;
wherein an end of said resecting member engages with a part of the fluid passage forming member and the other end of said resecting member engages with the movable part of the operation section.

18. A surgical instrument for endoscope, comprising:
an operation section having a base part and a movable part which is movable relative to the base part;
an elongated and flexible hollow member having a first end coupled to said operating section and a second end for insertion into a body cavity;
a flexible fluid passage forming member disposed in said hollow member to be slidable relative thereto, a tip end of the fluid passage forming member protruding from and retracting in the second end of the hollow member when the movable part of the operation section moves in the hollow member relative to the base part thereof; and
a resecting member disposed within the hollow member, at least one end of the resecting member being engageable with the movable part which moves relative to the base part of the operation section, the resecting member comprising a loop forming part when it protrudes from the hollow member;
wherein said base part of said operation section comprises a guide member extending from an operation section body in a longitudinal direction thereof and the movable part comprises a slider mounted on the guide member slidably in the longitudinal direction thereof;
wherein said hollow member comprises a tube-like sheath;
wherein said fluid passage forming member comprises a fluid injection needle and a tube member extending from the operation section to the second end of the hollow member, an end of said tube member is secured to the slider of the operation section and the other end of which fixedly connects the fluid injection needle; and
wherein one end of the resecting member is fixedly connected to the fluid injection needle.

19. An endoscope apparatus, comprising:
an endoscope operation section;
an insertion section coupled to the endoscope operation section for insertion in a body cavity;
an end structure section coupled to a tip end of the insertion section;
a forceps insert socket connecting to the insertion section; and
a surgical instrument engaging with the forceps insert socket, said surgical instrument comprising:
an operation section having a base part and a single movable part which is movable relative to the base part;
an elongated and flexible hollow member having a first end coupled to said operating section and a second end inserting into body cavity;
a flexible fluid passage forming member disposed in said hollow member to be slidable relative thereto, a tip end of the fluid passage forming member protruding from and retracting in the second end of the hollow member when the single movable part of the operation section moves in the hollow member relative to the base part thereof; and
a resecting member disposed within the hollow member, at least one end of the resecting member being engageable with the single movable part which moves relative to the base part of the operation section, the resecting member comprising a loop forming part when it protrudes from the hollow member;
wherein movement of the single movable part in a first direction protrudes both the tip end of the fluid passage and the resecting member from the hollow member and movement of the single movable part in a second direction retracts both the tip end of the fluid passage and the resecting member into the hollow member.

20. The endoscope apparatus according to claim 19, wherein:
said base part of said operation section comprises a guide member extending from an operation section body in a longitudinal direction thereof and the movable part comprises a slider mounted on the guide member slidably in the longitudinal direction thereof;
said hollow member comprises a tube-like sheath; and
said fluid passage forming member comprises a fluid injection needle and a tube member extending from the operation section to the second end of the hollow member, an end of said tube member is secured to the slider of the operation section and the other end of which fixedly connects the fluid injection needle.

21. The endoscope apparatus according to claim 19 or 20, wherein the resecting member comprises a metal wire.

22. The endoscope apparatus according to claim 21, wherein the wire is formed from a single wire.

23. The endoscope apparatus according to claim 21, wherein the wire is formed from a stranded wire.

24. The endoscope apparatus according to claim 21, wherein the wire connects to the fluid injection needle by brazing.

25. The endoscope apparatus according to claim 21, wherein the wire connects to the fluid injection needle by soldering.

26. The endoscope apparatus according to claim 21, wherein the wire connects to the fluid injection needle by adhesion by an adhesive.

27. The endoscope apparatus according to claim 21, wherein the wire is widely bent at the front end thereof to form a loop.

28. The endoscope apparatus according to claim 20, wherein the sheath is formed from an electrically insulating polymeric resin material.

29. The endoscope apparatus according to claim 20, wherein the sheath is formed from a polymeric resin.

30. The endoscope apparatus according to claim 19, wherein both ends of said resecting member engage with the movable part of the operation section.

31. The endoscope apparatus according to claim 19, wherein the resecting member comprises at least one slip-prevention member along the inside thereof.

32. The endoscope apparatus according to claim 31, wherein the slip-prevention member comprises a small pin provided at intervals.

33. The endoscope apparatus according to claim 31, wherein the slip-prevention member comprises a small needle provided at intervals.

34. The endoscope apparatus according to claim 19, wherein a high frequency energy is applied to the resecting member.

35. An endoscope apparatus, comprising:

an endoscope operation section;

an insertion section coupled to the endoscope operation section for insertion in a body cavity;

an end structure section coupled to a tip end of the insertion section;

a forceps insert socket connecting to the insertion section; and a surgical instrument engaging with the forceps insert socket, said surgical instrument comprising:
an operation section having a base part and a movable part which is movable relative to the base part;
an elongated and flexible hollow member having a first end coupled to said operating section and a second end inserting into body cavity;
a flexible fluid passage forming member disposed in said hollow member to be slidable relative thereto, a tip end of the fluid passage forming member protruding from and retracting in the second end of the hollow member when the movable part of the operation section moves in the hollow member relative to the base part thereof; and
a resecting member disposed within the hollow member, at least one end of the resecting member being engageable with the movable part which moves relative to the base part of the operation section, the resecting member comprising a loop forming part when it protrudes from the hollow member;
wherein an end of said resecting member engages with a part of the fluid passage forming member and the other end of which engages with the movable part of the operation section.

36. An endoscope apparatus, comprising:

an endoscope operation section;

an insertion section coupled to the endoscope operation section for insertion in a body cavity;

an end structure section coupled to a tip end of the insertion section;

a forceps insert socket connecting to the insertion section; and a surgical instrument engaging with the forceps insert socket, said surgical instrument comprising:
an operation section having a base part and a movable part which is movable relative to the base part;
an elongated and flexible hollow member having a first end coupled to said operating section and a second end inserting into body cavity;
a flexible fluid passage forming member disposed in said hollow member to be slidable relative thereto, a tip end of the fluid passage forming member protruding from and retracting in the second end of the hollow member when the movable part of the operation section moves in the hollow member relative to the base part thereof; and
a resecting member disposed within the hollow member, at least one end of the resecting member being engageable with the movable part which moves relative to the base part of the operation section, the resecting member comprising a loop forming part when it protrudes from the hollow member;
wherein said base part of said operation section comprises a guide member extending from an operation section body in a longitudinal direction thereof and the movable part comprises a slider mounted on the guide member slidably in the longitudinal direction thereof;
said hollow member comprises a tube-like sheath; and
said fluid passage forming member comprises a fluid injection needle and a tube member extending from the operation section to the second end of the hollow member, an end of said tube member is secured to the slider of the operation section and the other end of which fixedly connects the fluid injection needle; and
wherein one end of the resecting member is fixedly connected to the fluid injection needle.

* * * * *